United States Patent
Gurney et al.

(10) Patent No.: US 10,179,152 B2
(45) Date of Patent: Jan. 15, 2019

(54) THERAPY WITH CELLS FROM HUMAN PLACENTA AND HEMATOPOIETIC CELLS

(71) Applicant: Anthrogenesis Corporation, Warren, NJ (US)

(72) Inventors: Jodi P. Gurney, Chicago, IL (US); Xiaokui Zhang, Livingston, NJ (US); Stacy Herb, Mountain Top, PA (US); Robert J. Hariri, Bernardsville, NJ (US)

(73) Assignee: Celularity, Inc., Warren, NJ (US)

( * ) Notice: Subject to any disclaimer, the term of this patent is extended or adjusted under 35 U.S.C. 154(b) by 102 days.

(21) Appl. No.: 15/026,896

(22) PCT Filed: Oct. 2, 2014

(86) PCT No.: PCT/US2014/058774
§ 371 (c)(1),
(2) Date: Apr. 1, 2016

(87) PCT Pub. No.: WO2015/051088
PCT Pub. Date: Apr. 9, 2015

(65) Prior Publication Data
US 2016/0235790 A1 Aug. 18, 2016

Related U.S. Application Data

(60) Provisional application No. 61/886,648, filed on Oct. 3, 2013, provisional application No. 61/890,057, filed on Oct. 11, 2013.

(51) Int. Cl.
*A61K 35/50* (2015.01)
*A61K 35/51* (2015.01)
*A61K 35/12* (2015.01)
*A61K 35/28* (2015.01)
*C12N 5/0789* (2010.01)

(52) U.S. Cl.
CPC .............. *A61K 35/50* (2013.01); *A61K 35/12* (2013.01); *A61K 35/28* (2013.01); *A61K 35/51* (2013.01); *C12N 5/0647* (2013.01); *A61K 2035/122* (2013.01); *A61K 2035/124* (2013.01)

(58) Field of Classification Search
CPC ........ A61K 35/50; A61K 35/12; A61K 35/28; A61K 35/51; A61K 2035/122; A61K 2035/124
See application file for complete search history.

(56) References Cited

U.S. PATENT DOCUMENTS

2003/0032179 A1* 2/2003 Hariri .................... A61M 1/02
435/366
2004/0219136 A1* 11/2004 Hariri .................... A61K 35/44
424/93.71
2009/0252710 A1* 10/2009 Zhang ................... A61K 35/50
424/93.7

* cited by examiner

*Primary Examiner* — Kara D Johnson
(74) *Attorney, Agent, or Firm* — Celularity, Inc.; Timothy L. Smith; Geoffry T. Knudsen

(57) ABSTRACT

Provided herein are methods of treatment comprising administering to a subject, e.g., a human subject, mononuclear cells from human placental perfusate and hematopoietic cells, and compositions comprising them, and their uses to establish chimerism, engraft tissue (e.g., blood), reduce the severity or duration of graft versus host disease, and treat or ameliorate symptoms of metabolic disorders and hematologic disorders, such as hematologic malignancies.

20 Claims, No Drawings

THERAPY WITH CELLS FROM HUMAN PLACENTA AND HEMATOPOIETIC CELLS

This application claims benefit of U.S. Provisional Patent Application No. 61/890,057, filed Oct. 11, 2013 and U.S. Provisional Patent Application No. 61/886,648, filed Oct. 3, 2013, the disclosures of which are incorporated by reference herein in their entirety.

1. FIELD

Provided herein are methods of treatment comprising administering to a subject, e.g., a human subject, mononuclear cells from human placental perfusate and hematopoietic cells, and compositions comprising them, and their uses to establish chimerism, engraft tissue (e.g., blood), reduce the severity or duration of graft versus host disease, and treat or ameliorate symptoms of metabolic disorders and hematologic disorders, such as hematologic malignancies.

2. BACKGROUND

In allogeneic hematopoietic stem cell transplantation (HSCT), stem cells capable of reconstituting the immune system and forming blood cells (hematopoiesis) are transferred from one individual to another. Genotypically human leukocyte antigen (HLA)-identical related donors—which are available for about 30% of Caucasian patients—are regarded as the best donors for HSCT. Unfortunately, many patients do not have an available family or unrelated donor whose bone marrow is an identical match; their only curative option is to have a transplant from a partially matched, related donor (PMRD), which comes with the risk of graft-versus host disease (GVHD) and its complications, including transplant related mortality.

Umbilical cord blood (UCB) represents another source of cells suitable for use in HSCT. One of the advantages of UCB in this clinical setting is the reduced risk of GVHD. Unfortunately, current UCB cell transplant therapy also has drawbacks, including the limitation in the amount of cells that can be transplanted. Safety and efficacy may be compromised when transplant with a large number of UCB cells, e.g., greater than one unit, is required. Moreover, the risk of graft failure and GVHD is present, particularly when HLA-matching is incomplete. Another disadvantage to HSCT using UCB versus bone marrow or peripheral blood is a delay in the time to engraftment, which frequently results in recipient mortality.

Improvements in stem cell transplant therapies designed for hematopoietic reconstitution, therefore, are needed.

3. SUMMARY

In one aspect, provided herein are methods of transplanting hematopoietic cells to a subject, e.g., a human subject, comprising administering the hematopoietic cells in combination with mononuclear cells from human placental perfusate (HPCs), e.g., human placental perfusate. Sources of hematopoietic cells that can be used in the methods of transplanting hematopoietic cells described herein include, for example, bone marrow or cells therefrom, peripheral blood or cells therefrom, and umbilical cord blood or cells therefrom. As used herein, these sources of hematopoietic cells are collectively referred to as "HT cells."

In one aspect, provided herein is a method of transplanting HT cells, for example, human umbilical cord blood (UCB) cells to a subject, said method comprising administering HT cells, for example, UCB cells, in combination with a population of mononuclear cells from human placental perfusate, wherein said HT cells, for example, UCB cells, are not related to the subject. In one aspect, provided herein is a method of transplanting HT cells, for example, UCB cells, to a subject, said method comprising administering HT cells, for example, UCB cells, in combination with a population of mononuclear cells from human placental perfusate, wherein said cells from human placental perfusate are not related to the subject. In one aspect, provided herein is a method of transplanting HT cells, for example, UCB cells, to a subject, said method comprising administering HT cells, for example, UCB cells, in combination with a population of mononuclear cells from human placental perfusate, wherein said cells from human placental perfusate are not matched to the subject.

In one aspect, provided herein are hematopoietic cells for use in a method of treatment of a disease in a subject, wherein the method comprises administering said hematopoietic cells in combination with mononuclear cells from human placental perfusate, wherein the disease is a metabolic disorder or a symptom thereof; a hematologic disorder or malignancy or a symptom thereof; graft versus host disease; or a tumor. The hematopoietic cells may be bone marrow cells or cells therefrom, peripheral blood cells or cells therefrom, or UCB cells or cells therefrom. In one aspect, the UCB cells are not related to the subject. In one aspect, the mononuclear cells from human placental perfusate are not related to the subject. In one aspect, the mononuclear cells from human placental perfusate are not matched to the subject. The embodiments described hereinafter refer to each aspect disclosed.

In certain embodiments, the HT cells, for example, UCB cells, are not related to said mononuclear cells from placental perfusate. In certain embodiments, the HT cells, for example, UCB cells, are not matched to said mononuclear cells from placental perfusate. In certain embodiments, the HT cells, for example, UCB cells, are not related or matched to said mononuclear cells from placental perfusate. In particular embodiments, the HT cells, for example, UCB cells, are 3/6 to 6/6 HLA-matched to the subject. In particular embodiments, the HT cells, e.g., HT cells from an adult source, are 6/8 to 8/8 HLA-matched to the subject.

In certain embodiments, one unit of HT cells, for example, UCB cells, is administered. In other embodiments, greater than one unit of HT cells, for example, UCB cells, is administered. In particular embodiments, 2-6 units of HT cells, for example, UCB cells, are administered.

In certain embodiments, the HT cells, for example, UCB cells, are present in blood, e.g., UCB. In certain embodiments, the mononuclear cells from placental perfusate are present in placental perfusate.

In certain embodiments, the placental perfusate is obtained from a placenta that has been partially exsanguinated.

In certain embodiments, 2% or greater of the placental perfusate cells are CD34+.

In certain embodiments, the method results in chimerism in the subject. In particular embodiments, the chimerism comprises HT cells, for example, HT cells, for example, UCB cells, or progeny therefrom. In particular embodiments, greater than one unit of HT cells, for example, UCB cells, is administered and the method results in chimerism in the subject, and the chimerism comprises cells from greater than one unit of HT cells, for example, UCB cells, or progeny therefrom. In particular embodiments, the chimerism comprises placental perfusate cells or progeny therefrom. In particular embodiments, the chimerism comprises HT cells, for example, UCB cells, or progeny therefrom and placental perfusate cells or progeny therefrom.

In certain embodiments, the method results in engraftment of HT cells, for example, UCB cells. In particular embodiments, the method results in engraftment of placental perfusate cells.

In certain embodiments, the method reduces the duration or severity of graft versus host disease.

In certain embodiments, the subject has a tumor and the method results in a graft versus tumor reaction. In certain embodiments, the method results in tumor treatment.

In certain embodiments, the method results in amelioration of a symptom of a metabolic disorder such as adrenoleukodystrophy, mucopolysaccharidosis, Niemann-Pick disease, metachromatic leukodystrophy, Wolman disease, Krabbe's disease, Gaucher's disease, fucosidosis, or Batten disease in a subject in need thereof.

In certain embodiments, the method results in amelioration of a symptom of a hematologic disorder or malignancy, such as myelodysplastic syndrome, amegakaryocytic thrombocytopenia, acute lymphoblastic leukemia, acute myelogenous leukemia, sickle cell disease, beta thalassemia, severe combined immunodeficiency disease, marrow failure, or anemia such as severe aplastic anemia or Diamond-Blackfan anemia in a subject in need thereof.

In certain embodiments, the subject is a human subject. In certain embodiments, the human subject is 25 years old or younger. In specific embodiments, the human subject is an infant.

4. DETAILED DESCRIPTION

4.1. Method of Using Hematopoietic Cells, e.g., Umbilical Cord Blood Cells, and Cells from Human Placental Perfusate In one aspect, provided herein are methods of transplanting hematopoietic cells to a subject, e.g., a human subject, comprising administering the hematopoietic cells in combination with mononuclear cells from human placental perfusate (HPCs), e.g., human placental perfusate. Sources of hematopoietic cells that can be used in the methods of transplanting hematopoietic cells described herein include, for example, bone marrow or cells therefrom, peripheral blood or cells therefrom, and umbilical cord blood or cells therefrom. As used herein, these sources of hematopoietic cells are collectively referred to as "HT cells."

In one embodiment, provided herein is a method of transplanting HT cells, for example, human umbilical cord blood cells (UCB) cells, e.g., human umbilical cord blood, to a subject, e.g., a human subject, comprising administering the HT cells, for example, human umbilical cord blood cells (UCB) cells, e.g., human umbilical cord blood, in combination with mononuclear cells from human placental perfusate (HPCs), e.g., human placental perfusate. In one embodiment, the HT cells, for example, human UCB cells, e.g., human UCB, are not related to the subject. In a particular embodiment, the HT cells, for example, UCB cells, e.g., human UCB, are partially unmatched to the subject. In another embodiment, the HPCs, e.g., human placental perfusate, are not related to the subject. In a particular embodiment, the HPCs, e.g., human placental perfusate, are partially unmatched to the subject. In another particular embodiment, the HPCs, e.g., human placental perfusate, are not matched to the subject. In yet another embodiment, the HT cells, for example, human UCB cells, e.g., human UCB, are unrelated to the subject and the HPCs, e.g., human placental perfusate, are unrelated to the subject. In still another embodiment, the HT cells, for example, human UCB cells, e.g., human UCB, are unrelated and partially unmatched to the subject and the HPCs, e.g., human placental perfusate, are unrelated and partially unmatched or unmatched to the subject. In one embodiment HPCs, e.g., human placental perfusate, are unrelated and unmatched to the HT cells, for example, human UCB cells, e.g., UCB. In one embodiment HPCs, e.g. human placental perfusate, are unrelated and unmatched to the HT cells, for example, human UCB cells, e.g., UCB, and the recipient.

Unless otherwise noted, "related," as used herein in the context of UCB or HPCs, refers to self, or to a first or second degree blood relative. For example, UCB that is related to the subject refers to UCB from the subject itself, or from a first or second degree blood relative of the subject. In another example, UCB that is related to HPC refers to UCB and HPC that are from the same donor, or donors that are first or second degree blood relatives. Likewise, unless otherwise noted, "unrelated," in these contexts, refers to relationships that are more distant than that of a second degree blood relative.

Unless otherwise noted, "matched," as used herein in the context of UCB or cells from human placental perfusate (e.g., HPCs), refers to HLA matched. In addition, as used herein, "partially unmatched," as used herein in the context of UCB or cells from human placental perfusate (e.g., HPCs), refers to situations where there is matching at 3/6, 4/6, or 5/6 HLA loci, or in particular embodiments with respect to HT cells, e.g., from an adult source, refers to situations where there is matching at 6/8, 7/8, or 8/8 HLA loci. Also, unless otherwise noted, "unmatched," or "not matched," as used herein in the context of UCB or cells from human placental perfusate (e.g., HPCs), refers to matching at 0/6, 1/6, or 2/6 HLA loci, or in particular embodiments with respect to HT cells, e.g., from an adult source, refers to matching at 0/8, 1/8, 2/8, 3/8, 4/8, or 5/8 HLA loci. "Matched," "partially unmatched," and "unmatched" can, for example, refer to the relationship between the HT cells, for example, UCB cells, and HPCs, between units of HT cells, for example, UCB cells, and/or between the HT cells, for example, UCB cells, and/or HPCs and the subject that is the recipient of the cells.

Unless otherwise noted, a "unit," as used herein (e.g., in the context of transplantation), of UCB or cells thereform, refers to UCB or cells therefrom from a single umbilical cord. In certain embodiments, such methods comprise administering one unit of UCB, or cells therefrom. In another embodiment, the methods presented herein comprise administering multiple units of UCB, or cells therefrom. For example, the methods presented herein can comprise administering two, three, or four units of UCB, or cells therefrom. In instances wherein greater than one unit of HT cells, for example, UCB cells, is used, in certain embodiments, at least a portion of the HT cells, for example, UCB cells, can be unrelated to the subject, to the HPCs, and/or to other portions of the HT cells, for example, UCB cells (e.g., other UCB cell units). In instances wherein greater than one unit of HT cells, for example, UCB cells, is used, in certain embodiments, at least a portion of the HT cells, for example, UCB cells, can be unmatched or partially unmatched to the subject, to the HPCs, and/or to other portions of the HT cells, for example, UCB cells (e.g., other UCB cell units). In another embodiment, the methods presented herein can comprise administering less than one unit of HT cells or UCB, or cells therefrom. For example, the methods presented herein can comprise administering 0.2, 0.3, 0.4, 0.5, 0.6, 0.7, 0.8, or 0.9 units of HT cells or UCB, or cells therefrom. In particular embodiments, the methods presented herein can comprise administering a particular number of units (less than one, one, or more than one) over multiple administrations.

In another aspect, provided herein are methods for inducing chimerism in a subject, comprising administering to the subject a combination of HT cells, for example, UCB cells, e.g., UCB, and HPCs, e.g., human placental perfusate, wherein at least a portion of the HT cells, for example, UCB cells, are partially unmatched to the subject, and/or the HPCs are unmatched or partially unmatched to the subject, such that chimerism in the subject occurs. "Chimerism," unless noted otherwise, as used herein, refers to the presence in a subject of non-self DNA, e.g., the presence of DNA from cells that are unmatched or partially unmatched relative to the recipient subject.

In one embodiment of such methods, greater than one unit of HT cells, for example, UCB cells, is administered to the subject, e.g., 2, 3, or 4 units of HT cells, for example, UCB cells, are administered to the subject. In particular embodiments wherein greater than one unit of HT cells, for example, UCB cells, is administered to the subject the method of inducing chimerism can result in multiple chimerism, that is, chimerism involving greater than one, and up to all, of the administered HT cell, e.g., UCB cell, units, or progeny thereof, can result.

In another embodiment of such methods, chimerism involving the HPCs or progeny thereof can result. In yet another embodiment, chimerism involving the HT cells, for example, UCB cells (including multiple chimerism in instances wherein greater than one unit of HT cells, for example, UCB cells, is administered), or progeny thereof, and the HPCs, or progeny thereof, can result.

In still yet another embodiment of such methods, the HT cells, for example, UCB cells, are unrelated to the subject. In instances in which greater than one unit of HT cells, e.g., UCB, is administered, one or more of the HT cell, e.g., UCB cell, units can be unrelated to the subject. In a particular embodiment of such methods, the HPCs are unrelated to the subject and can, additionally, be unrelated to the HT cells, for example, UCB cells. In still another embodiment of such methods, both the HT cells, for example, UCB cells, and the HPCs are unrelated to the subject.

In certain embodiments of such methods, chimerism (comprising either or both HT cells, for example, UCB cells, or progeny thereof, or HPCs, or progeny thereof) is first detected in the subject within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 days, or more of administration of the HT cells, for example, UCB cells, in combination with the HPCs to the subject.

Chimerism can be detected using methods known in the art. For example, chimerism can be detected using blood samples. In one embodiment, chimerism is detected using a polymerase chain reaction (PCR)-based method, e.g., by short tandem repeat assays. In one embodiment, a test for chimerism after a hematopoietic stem cell transplant involves identifying the genetic profiles of the recipient and of the donor and then evaluating the extent of mixture in the recipient's blood, bone marrow, or other tissue. Chimerism testing (engraftment analysis) by DNA employs methodology commonly used in human identity testing and is accomplished by the analysis of genomic polymorphisms called short tandem repeat (STR) loci. In one embodiment, quantitation (e.g., using short tandem repeat assays) of peripheral blood donor chimerism (UCB/s and perfusate cells)(whole blood, NK and T Cell) is assessed on Days 7, 14, 30, 60, 100 and 180 (+/−10 days), with quantitation (e.g., using short tandem repeat assays) of peripheral blood recipient chimerism assessed at baseline along with chimerism of the donor cells (UCB and perfusate cells) at baseline.

In still another aspect, provided herein are methods for cell engraftment, e.g., platelet or neutrophil engraftment, in a subject, comprising administering to the subject a combination of HT cells, for example, human UCB cells, e.g., UCB, and HPCs, e.g., human placental perfusate, wherein at least a portion of the HT cells, for example, UCB cells, are partially matched to the subject, and/or the HPCs are unmatched or partially unmatched to the subject, such that cell engraftment in the subject occurs. In certain embodiments, the cell engraftment comprises engraftment of HT cells, for example, UCB cells, or progeny thereof. In certain other embodiments, the cell engraftment comprises engraftment of HPCs, or progeny thereof. In still other embodiments, the engraftment comprises engraftment of HT cells, for example, UCB cells, or progeny thereof, and HPCs, or progeny thereof. In certain embodiments, a method of cell engraftment provided herein shortens the time to engraftment.

In one embodiment of such methods, the HT cells, for example, UCB cells, are unrelated to the subject. In a particular embodiment, the HT cells, for example, UCB cells, are partially unmatched to the subject. In another particular embodiment, the HPCs are unrelated to the subject and can, additionally, be unrelated to the HT cells, for example, UCB cells. In a particular embodiment, the HPCs are partially unmatched to the subject. In another particular embodiment, the HPCs are not matched to the subject. In yet another embodiment, the UCB cell are unrelated to the subject and the HPCs are unrelated to the subject. In still another embodiment, the HT cells, for example, UCB cells, are unrelated and partially unmatched to the subject and the HPCs are unrelated and partially unmatched or unmatched to the subject. In certain embodiments, the methods presented herein exhibit an enhanced ability to engraft as compared to administration of HT cells, for example, UCB cells, alone.

Engraftment can be detected using methods known in the art. For example, in one embodiment, a complete blood count with differential may be performed every 1-3 days from Day 0 to absolute neutrophil count >500/mm$^3$ for 3 days after nadir is reached and until platelet count reaches ≥20,000/mm$^3$ for 3 consecutive measurements on 3 different days and independence from platelet transfusion for a minimum of 7 days. As used herein, "neutrophil engraftment" refers to the first of three days following the neutrophil nadir with an absolute neutrophil count above 500/mm$^3$. As used herein, "platelet engraftment" refers to the first of three consecutive days demonstrating a platelet count ≥20,000/mm$^3$, after a seven day period of platelets ≥20,000/mm$^3$ without transfusions.

In certain embodiments, cell engraftment in the subject is detected within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 days, or 2 months, 2.5 months, 3 months, or more of administration of the HT cells, for example, UCB cells, in combination with HPCs to the subject.

In certain embodiments, the methods presented herein comprise administering one unit of HT cells, for example, UCB cells, e.g., UCB. In another embodiment, the methods presented herein comprise administering multiple units of HT cells, for example, UCB cells, e.g., UCB. For example, the methods presented herein can comprise administering two, three, or four units of HT cells, for example, UCB cells, e.g., UCB.

In still another aspect, provided herein are methods for reducing the duration or severity of GVHD in a subject, comprising administering to the subject a combination of HT cells, for example, human UCB cells, e.g., UCB, and HPCs, e.g., human placental perfusate, wherein at least a portion of the HT cells, e.g., UCB cells, are partially matched to the subject, and/or the HPCs are unmatched or partially unmatched to the subject, such that a reduction in the duration or severity of GVHD in the subject occurs.

In one embodiment of such methods, the HT cells, for example, UCB cells, are unrelated to the subject. In a particular embodiment, the HT cells, for example, UCB cells, are partially unmatched to the subject. In another particular embodiment, the HPCs are unrelated to the subject and can, additionally, be unrelated to the HT cells, for example, UCB cells. In a particular embodiment, the HPCs are partially unmatched to the subject. In another particular embodiment, the HPCs are not matched to the subject. In yet another embodiment, the HT cells, for example, UCB cells, are unrelated to the subject and the HPCs are unrelated to the subject. In still another embodiment, the HT cells, for example, UCB cells, are unrelated and partially unmatched to the subject and the HPCs are unrelated and partially unmatched or unmatched to the subject. In certain embodiments, the methods presented herein exhibit reduced severity or duration of GVHD as compared to administration of HT cells, for example, UCB cells, alone.

In certain embodiments, the methods presented herein comprise administering one unit of HT cells, for example, UCB cells, e.g., UCB. In another embodiment, the methods presented herein comprise administering multiple units of HT cells, for example, UCB cells, e.g., UCB. For example, the methods presented herein can comprise administering two, three, or four units of HT cells, for example, UCB cells, e.g., UCB.

In certain embodiments, the methods presented herein comprise administering HT cells, for example, UCB cells, e.g., UCB, concurrently with the HPCs, e.g., human placental perfusate. In a particular embodiment, the cells are administered to a subject simultaneously. In another embodiment, the HT cells, for example, UCB cells, and HPCs are administered to the subject within 0.5, 1, 1.5, 2, 3, 4, 6, 8, 10, 12, 16, 18, or 24 hours or more, or within 1, 2, 3, 4, 5, 6, or 7 days or more of each other. In a specific embodiment, the HT cells, for example, UCB cells, e.g., UCB, is administered to the subject, then the HPC, e.g., human placental perfusate, is administered, e.g., is administered within 1 hour of administration of UCB, or within the minimum period necessary to verify that the subject is not exhibiting an adverse reaction to the UCB administration.

The methods provided herein can exhibit advantages that can include, for example, a reduction in the length of time to cell engraftment, limiting the time the subject is neutropenic, limiting the time the subject is thrombocytopenic, establishment of chimerism, and reducing the severity or duration of, or preventing, GVHD, relative to administration of HT cells, for example, UCB cells, e.g., UCB, alone.

The ratio of HT cells, for example, UCB cells, and HPCs administered can vary. The ratio of HT cells, for example, UCB cells, and HPCs can be determined according to the judgment of those of skill in the art. In certain embodiments, the ratio of HT cells, for example, UCB cells, to HPCs is about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000. In certain embodiments, the ratio of HT cells, for example, UCB cells, to HPCs is between about 20:1 and about 1:20, or is about 1:10, about 1:5, about 1:1, about 5:1 or about 10:1.

Administration of HT cells, for example, UCB cells, and HPCs can be performed using any technique for cell administration known in the art. In one embodiment, administration is venous, for example, intravenous, e.g., through an IV, PICC line, central line, etc. For example, HT cells, for example, UCB cells, and HPCs may be administered, in separate compositions or in a single composition, to a subject in any pharmaceutically or medically acceptable manner, including by injection or transfusion. In certain embodiments, the composition(s) may be formulated as an injectable composition (e.g., WO 96/39101, incorporated herein by reference in its entirety).

In certain embodiments, HT cells, for example, UCB cells, or HPCs are administered to a subject parenterally. The term "parenteral" as used herein includes subcutaneous injections, intravenous, intramuscular, intra-arterial injection, or infusion techniques. In certain embodiments, HT cells, for example, UCB cells, or HPCs are administered to a subject intravenously. In certain other embodiments HT cells, for example, UCB cells, or HPCs are administered to a subject intraventricularly.

HT cells, for example, UCB cells, and HPCs may be contained, separately or together, in any pharmaceutically-acceptable carrier. The HT cells, for example, UCB cells, or HPCs may be carried, stored, or transported in any pharmaceutically or medically acceptable container, for example, a blood bag, transfer bag, plastic tube, syringe, vial, or the like.

Administration of HT cells, for example, UCB cells, and/or HPCs to a subject can be performed once or a plurality of times. In certain embodiments, administration is performed once. In certain embodiments, administration is performed a plurality of times, e.g., two, three, four, or more times. In certain embodiments, HT cells, for example, UCB cells, are administered a plurality of times. In certain embodiments, HPCs are administered a plurality of times.

In certain embodiments, the amount of cord blood or cells obtained therefrom (e.g., total nucleated cells from umbilical cord blood) administered to a subject in accordance with the methods described herein can be determined based on the number of cells present in the cord blood. The amount or number of UCB or cells obtained therefrom (e.g., total nucleated cells from umbilical cord blood) and/or human placental perfusate or HPCs or total nucleated cells obtained therefrom administered to the subject depends on the source of umbilical cord blood or cells obtained therefrom (e.g., total nucleated cells from umbilical cord blood) and/or human placental perfusate or HPCs or total nucleated cells obtained therefrom, the severity or nature of disorders or conditions to be treated, as well as age, body weight and physical condition of the subject, etc. In certain embodiments, about 0.01 to about 0.1, about 0.1 to about 1, about 1 to about 10, about 10 to about $10^2$, about $10^2$ to about $10^3$, about $10^3$ to about $10^4$, about $10^4$ to about $10^5$, about $10^5$ to about $10^6$, about $10^6$ to about $10^7$, about $10^7$ to about $10^8$, or about $10^8$ to about $10^9$ umbilical cord blood cells (e.g., total nucleated cells from umbilical cord blood), human placental perfusate or cells obtained therefrom (e.g., HPCs or total nucleated cells from placental perfusate), or total umbilical cord blood cells and cells obtained from placental perfusate (e.g., HPCs or total nucleated cells) per kilogram body weight of a subject are administered. In various embodiments, at least about 0.1, 1, 10, $10^2$, $10^3$, $10^4$, $10^5$, $10^6$, $10^7$, $10^8$, or $10^9$ umbilical cord blood cells (e.g., total nucleated cells from umbilical cord blood), cells obtained from placental perfusate (e.g., HPCs or total nucleated cells from placental perfusate), or umbilical cord blood cells and cells obtained from placental perfusate per kilogram body weight of a subject are administered.

In specific embodiments, at least about $0.5 \times 10^6$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$, $1.0 \times 10^7$, $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, or $6.0 \times 10^7$ umbilical cord blood cells (e.g., total nucleated cells from umbilical cord blood), cells obtained from placental perfusate (e.g., HPCs or total nucleated cells from placental perfusate), or umbilical cord blood cells and cells obtained from placental perfusate (e.g., HPCs or total nucleated cells from placental perfusate) per kilogram body weight of a subject are administered. In a more specific embodiment, at least about $0.5 \times 10^6$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, or $5.0 \times 10^6$ cells obtained from placental perfusate (e.g., HPCs or total nucleated cells from placental perfusate) per kilogram body weight of a subject are administered. In a more specific embodiment, at least about $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, or $6.0 \times 10^7$ umbilical cord blood cells (e.g., total nucleated cells from umbilical cord blood) per kilogram body weight of a subject are administered. In various embodiments, at most about $10^4$, $10^5$, $10^6$, $10^7$, $10^8$, or $10^9$ umbilical cord blood cells, cells obtained from placental perfusate (e.g., HPCs or total nucleated cells from placental perfusate), or umbilical cord blood cells and cells obtained from placental perfusate (e.g., HPCs or total nucleated cells from placental perfusate) per kilogram body weight of a subject are administered. In specific embodiments, at most about $0.5 \times 10^6$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$, $1.0 \times 10^7$, $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, or $6.0 \times 10^7$ umbilical cord blood cells (e.g., total nucleated cells from umbilical cord blood), cells obtained from placental perfusate (e.g., HPCs or total nucleated cells from placental perfusate), or umbilical cord blood cells and cells obtained from placental perfusate (e.g., HPCs or total nucleated cells from placental perfusate) per kilogram body weight of a subject are administered. In a more specific embodiment, at most about $0.5 \times 10^6$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, or $5.0 \times 10^6$ cells obtained from placental perfusate (e.g., HPCs or total nucleated cells from placental perfusate) per kilogram body weight of a subject are administered. In a more specific embodiment, at most about $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, or $6.0 \times 10^7$ umbilical cord blood cells (e.g., total nucleated cells from umbilical cord blood) per kilogram body weight of a subject are administered. In specific embodiments, a greater number of umbilical cord blood cells (e.g., total nucleated cells from umbilical cord blood) than cells obtained from placental perfusate (e.g., HPCs or total nucleated cells from placental perfusate) per kilogram body weight of a subject are administered.

In specific embodiments, a greater number of HT cells, for example, umbilical cord blood cells (e.g., total nucleated HT cells, for example, cells from umbilical cord blood) than cells obtained from placental perfusate (e.g., HPCs or total nucleated cells from placental perfusate) per kilogram body weight of a subject are administered.

In certain embodiments, at least about $10^4$ to about $10^7$, for example, $0.5 \times 10^4$, $1.0 \times 10^4$, $1.5 \times 10^4$, $2.0 \times 10^4$, $2.5 \times 10^4$, $3.0 \times 10^4$, $3.5 \times 10^4$, $4.0 \times 10^4$, $4.5 \times 10^4$, $5.0 \times 10^4$, $5.5 \times 10^4$, $6.0 \times 10^4$, $6.5 \times 10^4$, $7.0 \times 10^4$, $7.5 \times 10^4$, $8.0 \times 10^4$, $8.5 \times 10^4$, $9.0 \times 10^4$, $9.5 \times 10^4$, $0.5 \times 10^5$, $1.0 \times 10^5$, $1.5 \times 10^5$, $2.0 \times 10^5$, $2.5 \times 10^5$, $3.0 \times 10^5$, $3.5 \times 10^5$, $4.0 \times 10^5$, $4.5 \times 10^5$, $5.0 \times 10^5$, $5.5 \times 10^5$, $6.0 \times 10^5$, $6.5 \times 10^5$, $7.0 \times 10^5$, $7.5 \times 10^5$, $8.0 \times 10^5$, $8.5 \times 10^5$, $9.0 \times 10^5$, $9.5 \times 10^5$, $0.5 \times 10^6$, $1.0 \times 10^6$, $1.5 \times 10^6$, $2.0 \times 10^6$, $2.5 \times 10^6$, $3.0 \times 10^6$, $3.5 \times 10^6$, $4.0 \times 10^6$, $4.5 \times 10^6$, $5.0 \times 10^6$, $5.5 \times 10^6$, $6.0 \times 10^6$, $6.5 \times 10^6$, $7.0 \times 10^6$, $7.5 \times 10^6$, $8.0 \times 10^6$, $8.5 \times 10^6$, $9.0 \times 10^6$, $9.5 \times 10^6$, $1.0 \times 10^7$, $1.5 \times 10^7$, $2.0 \times 10^7$, $2.5 \times 10^7$, $3.0 \times 10^7$, $3.5 \times 10^7$, $4.0 \times 10^7$, $4.5 \times 10^7$, $5.0 \times 10^7$, $5.5 \times 10^7$, or $6.0 \times 10^7$, CD34+ cells per kilogram body weight are administered. Such CD34+ cells can be from cord blood alone, or can be from cord blood and placental perfusate. In certain embodiments, when the CD34+ cells are from cord blood and placental perfusate, the percentage of CD34+ cells from placental perfusate relative to total placental perfusate cells is greater than the percentage of CD34+ cells from cord blood relative to total cord blood cells. In one embodiment, the proportion of CD34+ cells in the placental perfusate cell population is 0.1-0.5, 0.5-1.0, 1.0-1.5, 1.5-2.0, 2.0-2.5, 2.5-3.0, 3.0-3.5, 3.5-4.0, 4.0-4.5, 4.5-5.0, 5.0-5.5, 5.5-6.0, 6.0-65, 6.5-7.0, 7.0-7.5, 7.5-8.0, 8.0-8.5, 8.5-9.0, 9.0-9.5, or 9.5-10.0 fold or higher compared to the proportion of CD34+ cells in the cord blood cell population. In certain embodiments, 0.1%, 0.5%, 1.0%, 1.5%, 2.0%, 2.5%, 3.0%, 3.5%, 4.0%, 4.5%, or 5.0% or greater of the placental perfusate cells are CD34+.

The HT cells, for example, UCB cells, e.g., UCB, and HPCs, e.g., placental perfusate, can be delivered in a volume appropriate for the size of the subject. Typical blood volume of a human adult is about 85-100 mL/kg body weight. Thus, the blood volume for human adults ranges from approximately 40 mL to approximately 300 mL. In various embodiments, therefore, HT cells, for example, UCB cells, e.g., UCB, and HPCs, e.g., placental perfusate is administered in a total volume of about 0.5 mL, 1.0 mL, 2 mL, 3 mL, 4 mL, 5 mL, 6 mL, 7 mL, 8 mL, 9 mL, 10 mL, 11 mL, 12 mL, 13 mL, 14 mL, 15 mL, 16 mL, 17 mL, 18 mL, 19 mL, 20 mL, 21 mL, 22 mL, 23 mL, 24 mL, 25 mL, 26 mL, 27 mL, 28 mL, 29 mL, or about 30 mL, or more. The administration of such volumes can be a single administration or in multiple administrations. The time over which such volumes of cord blood or number of cord blood cells, or human placental perfusate or cells obtained therefrom (e.g., HPCs or total nucleated cells from placental perfusate) can be administered can vary from, e.g., 0.5 hours, 1 hour, 1.5 hours, 2 hours, 2.5 hours, 3 hours, 3.5 hours, 4 hours, or more.

In certain embodiments, small transfusions under 20 mL are performed using a syringe. Larger-volume transfusions can administered by an infusion device, e.g., within a period of one to four hours.

The methods provided herein can be performed on any subject in need thereof. In one aspect, the subject is in need of hematopoietic reconstitution, partial reconstitution, or augmentation. In certain embodiments, the subject is a human subject. In certain embodiments, the subject is an adult human subject. In certain embodiments, the subject is 25 years or younger. In certain embodiments, the subject is an infant.

In certain embodiments, prior to the methods presented herein, e.g., methods of transplanting, inducing chimerism and/or methods of engraftment, the subject has been administered one or more of myeloablative conditioning, using, e.g., TBI, Clofarabine, and/or Ara-C1; reduced toxicity conditioning (also referred to as reduced intensity conditioning) using, e.g., Busulfan, Fludarabine, and/or Alemtuzumab; radiation therapy; chemotherapy; or other therapy such as immunosuppressive therapy or a therapy that reduces blood cell count. In a particular embodiment, wherein a subject has received one or more of the above, the subject exhibits complete myeloablation. In one embodiment, at least some immune system function is retained.

In a particular aspect, the methods provided herein can be used as methods for the treatment of a metabolic disorder such as an inborn error of metabolism, adrenoleukodystrophy, mucopolysaccharidosis, Niemann-Pick disease, metachromatic leukodystrophy, Wolman disease, Krabbe's disease, Gaucher's disease, fucosidosis, or Batten disease in a subject in need thereof.

In another particular aspect, the methods provided herein can be used as methods for the treatment of a hematologic disorder or malignancy, e.g., a lymphohematopoietic malignancy, myelodysplastic syndrome, amegakaryocytic thrombocytopenia, leukemias such as acute lymphoblastic leukemia (ALL) and acute myelogenous leukemia (AML), neutropenia, sickle cell disease such as sickle cell anemia, beta thalassemia (e.g. beta thalassemia major), severe combined immunodeficiency disease, marrow failure, or anemia such as severe aplastic anemia or Diamond-Blackfan anemia in a subject in need thereof.

As used herein, the terms "treat," "treating," and "treatment" refer to the reduction or amelioration of the progression, severity, and/or duration, of a disorder or condition, or any parameter or symptom of such a disorder or condition. Treatment may be considered efficacious if the subject survives, or if the disorder or condition to be treated is measurably improved in any way as a result of the treatment. Such improvement may be shown by, e.g., one or more measurable indicators including, for example, detectable changes in a physiological condition or set of physiological conditions associated with a particular disease, disorder or condition. Treatment is also considered effective if one or more indicators appears to respond to such treatment by changing to a value that is within, or closer to, a normal value for, e.g. individuals of similar age, than such indicator(s) would be expected to lie in the absence of the treatment.

In certain embodiments of the methods provided herein, the methods provided herein can be used as a first therapy in combination with one or more second therapies in the treatment of a disorder or condition. Such second therapies include, but are not limited to, surgery, hormone therapy, immunotherapy, phototherapy, or treatment with certain drugs. Exemplary therapies that can be used in combination with the methods provided herein include control of environmental temperature; support with oxygen; a respirator or a ventilator; peripheral blood transfusion; iron supplementation; intravenous feeding; phototherapy; surgery; agents for the treatment of metabolic disorders or hematologic disorders (including hematologic tumors); antibiotics or antiviral drugs; anti-inflammatory agents (e.g., steroidal anti-inflammatory compounds, non-steroidal anti-inflammatory (NSAID) compounds); nitric oxide; antihistamines; immune suppressants; and immunomodulatory compounds (e.g., a TNF-α inhibitor).

4.2. Human Placental Perfusate Cells

Mononuclear cells from human placental perfusate (HPCs), e.g., human placental perfusate, for use in accordance with the present disclosure may be collected in any medically or pharmaceutically-acceptable manner and may be present in a composition, e.g., a pharmaceutical composition. In certain embodiments, a composition (e.g., a pharmaceutical composition, i.e., a pharmaceutical grade solution suitable for administration to a human) provided herein comprises human placental perfusate. In certain embodiments, the composition comprises human placental perfusate obtained from partially exsanguinated placenta. In certain embodiments, the composition comprises human placental perfusate obtained from exsanguinated placenta. In certain embodiments, the composition comprises cells, such as stem cells, isolated from human placental perfusate. In certain embodiments, the composition comprises nucleated cells isolated from human placental perfusate, e.g., mononuclear cells or total nucleated cells.

In one embodiment, the HPCs, e.g., human placental perfusate, are sterile. In one embodiment, the population of HPCs, e.g., human placental perfusate, is heterogeneous.

In a specific embodiment, HPCs or human placental perfusate are processed by removal of red blood cells and/or granulocytes according to standard methods to produce a population of nucleated cells. Such enriched populations of cells may be used unfrozen, or may be frozen for later use. If the population of cells is to be frozen, a standard cryopreservative (e.g., DMSO, glycerol, Epilife™ Cell Freezing Medium (Cascade Biologics) can be added to the enriched population of cells before it is frozen.

In certain embodiments, cells obtained from placental perfusate comprise mononuclear cells from placental perfusate. In certain embodiments, cells obtained from placental perfusate comprise total nucleated cells from placental perfusate. In certain embodiments, the cells obtained from placental perfusate are obtained from a single placenta. In certain embodiments, the cells obtained from placental perfusate are obtained from more than one placenta. In certain embodiments, the cells obtained from placental perfusate are obtained from two placentas. In embodiments wherein the cells are obtained from greater than one placenta, the cells from the different placentas need not be related or matched to each other.

As described herein, placental perfusate may be obtained from a placenta that has been drained of cord blood and perfused to remove residual blood, prior to perfusion to obtain placental cells. Placental perfusate may be obtained from a placenta that has been drained of cord blood but not perfused to remove residual blood. Placental perfusate may be obtained from a placenta that has been separated from all but 0.5-6.0 inches, e.g., 0.5-1.0, 1.0-1.5, 1.5-2.0, 2.0-2.5, 2.5-3.0, 3.0-3.5, 3.5-4.0, or 4.0-6.0 inches, of the umbilical cord, wherein the umbilical cord may contain residual cord blood, a portion of which may enter the placental perfusate during perfusion and thus is comprised in the placental perfusate. Placental perfusate may be obtained from a placenta that has neither been drained of cord blood nor perfused to remove residual blood. In the latter two embodiments, the placental cells, e.g., nucleated cells from placental perfusate, for example, HPCs, comprise nucleated cells from placental blood and/or cord blood. In a specific embodiment, placental perfusate used in accordance with the present disclosure is free of umbilical cord blood. In another specific embodiment, placental perfusate used in accordance with the present disclosure is substantially free of umbilical cord blood, e.g., said placental perfusate comprises less than 10%, less than 5%, less than 1%, less than 0.5%, or less than 0.1% cord blood. Generally, where cells from perfusate comprise cord blood cells, such cells are considered part of the HPC population, not part of the HT cells, for example, UCB cells, for purposes of the methods provided herein.

Placental perfusate may be collected from a single individual (i.e., as a single unit) for administration, or may be pooled with other units, e.g., from the same individual or from one or more other individuals. In certain embodiments, the placental perfusate or cells obtained therefrom is stored prior to administration. In certain embodiments, a unit of placental perfusate contains a sufficient number of cells such that at least about $0.5 \times 10^6$, $1.0 \times 10^6$, $1.5 \times 10^6$, $2.0 \times 10^6$, $2.5 \times 10^6$, or $3.0 \times 10^6$ cells obtained from placental perfusate, e.g., total nucleated cells, per kilogram body weight of a subject are administered. In certain embodiments, one unit of placental perfusate or cells obtained therefrom is administered. In certain embodiments, less than one unit is administered. In certain embodiments, more than one unit is administered.

Placentas for obtaining placental perfusate can be recovered following successful birth and placental expulsion. In certain embodiments, the placenta is from a full-term birth. In certain embodiments, the placenta is from a premature birth. In some embodiments, the placenta is the placenta of an infant born at about 23 to about 25 weeks of gestation. In some embodiments, the placenta is the placenta of an infant born at about 26 to about 29 weeks of gestation. In some embodiments, the placenta is the placenta of an infant born at about 30 to about 33 weeks of gestation. In some embodiments, the placenta is the placenta of an infant born at about 34 to about 37 weeks of gestation. In some embodiments, the placenta is the placenta of an infant born at about 37 to about 42 weeks of gestation.

Human placental perfusate or cells obtained therefrom for use in accordance with the present disclosure are generally unrelated to the subject recipient of the cells. Human placental perfusate or cells obtained therefrom for use in accordance with the present disclosure are generally unmatched or partially unmatched to the subject recipient of the cells.

Human placental perfusate or cells obtained therefrom for use in accordance with the present disclosure can be obtained by any method. Placental perfusate can be obtained, e.g., as disclosed in U.S. Pat. No. 7,045,148, U.S. Pat. No. 7,255,879, and/or U.S. Pat. No. 8,057,788, the contents of each of which are incorporated herein by reference in their entirety. Such perfusion can, e.g., be perfusion by the pan method, wherein perfusion liquid is forced through the placental vasculature and perfusion fluid that exudes from the placenta, typically the maternal side, is collected in a pan containing the placenta. Perfusion can also, e.g., be a closed-circuit perfusion, wherein perfusion fluid is passed through, and collected from, only the fetal vasculature of the placenta. See, e.g., U.S. Pat. No. 8,057,788, the contents of which are incorporated herein by reference in their entirety. In a specific embodiment, such perfusion can be continuous, that is, perfusion fluid that has been passed through the placenta is passed through a second time, or a plurality of times, prior to isolation of cells obtained from placental perfusate (e.g., HPCs or total nucleated cells from placental perfusate).

4.3. Umbilical Cord Blood Cells

Umbilical cord blood (also referred to herein as UCB or "cord blood") for use in accordance with the present disclosure may be collected in any medically or pharmaceutically-acceptable manner and may be present in a composition, e.g., a pharmaceutical composition. Various methods for the collection of cord blood have been described. See, e.g., U.S. Pat. No. 6,102,871; U.S. Pat. No. 6,179,819; and U.S. Pat. No. 7,147,626, the contents of each of which are incorporated by reference in its entirety. A conventional technique for the collection of cord blood is based on the use of a needle or cannula, which is used with the aid of gravity. Cord blood may be collected into, for example, blood bags, transfer bags, or sterile plastic tubes.

In some embodiments, umbilical cord blood is obtained from a commercial cord blood bank (e.g., LifeBankUSA, etc.). In another embodiments, umbilical cord blood is collected from a post-partum mammalian umbilical cord and used immediately (e.g., within 1, 2, 3, 4, 5, 6, 7, 8, 9, 10, 11, or 12 hours of collection). In other embodiments, the cord blood used to treat a subject is cord blood that has been cryopreserved. Umbilical cord blood can be collected from a single umbilical cord or from a plurality of umbilical cords.

In certain embodiments, the HT cells, for example, UCB cells, are unrelated to the subject and/or the HPCs. In another embodiment, the HT cells, for example, UCB cells, are partially unmatched to the subject and/or the HPCs. In yet another embodiment, the HT cells, for example, UCB cells, are unmatched to the HPCs. In still another embodiment, the HT cells, for example, UCB cells, are unrelated and unmatched to the HPCs. In particular embodiments the UCB is matched to the subject at 3/6, 4/6, or 5/6 HLA loci. In particular embodiments the HT cells, e.g., from an adult source, are matched to the subject at 6/8, 7/8, or 8/8 HLA loci.

In some embodiments, umbilical cord blood is prepared from preterm umbilical cord. In other embodiments, umbilical cord blood is prepared from full-term umbilical cord. In certain embodiments, umbilical cord blood is obtained from a post-partum mammalian umbilical cord of a full-term birth. In other embodiments, umbilical cord blood is obtained from a post-partum mammalian umbilical cord of a premature birth. In some embodiments, the umbilical cord is the umbilical cord of an infant born at about 23 to about 25 weeks of gestation. In some embodiments, the umbilical cord is the umbilical cord of an infant born at about 26 to about 29 weeks of gestation. In some embodiments, the umbilical cord is the umbilical cord of an infant born at about 30 to about 33 weeks of gestation. In some embodiments, the umbilical cord is the umbilical cord of an infant born at about 34 to about 37 weeks of gestation. In some embodiments, the umbilical cord is the umbilical cord of an infant born at about 37 to about 42 weeks of gestation.

Cord blood, or cells obtained therefrom (e.g., total nucleated cells or stem cells derived therefrom), may be collected from a single individual (i.e., as a single unit) for administration, or may be pooled with other units. In certain embodiments, the cord blood, or cells obtained therefrom (e.g., total nucleated cells or stem cells derived therefrom) is stored prior to use. Where umbilical cord blood is pooled from a plurality of umbilical cords, the pooled cord blood can comprise umbilical cord blood from full-term births only, cord blood from a combination of full-term births, or cord blood from premature births only. For example, cord blood from the umbilical cord of a premature infant can be combined with, e.g., cord blood from other premature infants, cord blood from full-term births only, or a combination of cord blood from both premature and full-term placentas. Cord blood, including autologous or allogeneic cord blood, can also be combined with peripheral blood. In certain embodiments, cord blood from premature births is used, as such cord blood comprises relatively high numbers of CD34+ stem cells per unit volume, compared to cord blood from full-term births. In certain embodiments, a unit of cord blood contains a sufficient number of cells such that at least about $1.0\times10^6$, $1.5\times10^6$, $2.0\times10^6$, $1.5\times10^6$, $2.0\times10^6$, $2.5\times10^6$, $3.0\times10^6$, $3.5\times10^6$, $4.0\times10^6$, $4.5\times10^6$, $6.0\times10^6$, $6.5\times10^6$, $7.0\times10^6$, $7.5\times10^6$, $8.0\times10^6$, $8.5\times10^6$, $9.0\times10^6$, $9.5\times10^6$, $1.0\times10^7$, $1.5\times10^7$, $2.0\times10^7$, $2.5\times10^7$, $3.0\times10^7$, $3.5\times10^7$, $4.0\times10^7$, $4.5\times10^7$, $5.0\times10^7$, $5.5\times10^7$, or $6.0\times10^7$ cells obtained from said cord blood, e.g., total nucleated cells from cord blood, per kilogram body weight of a subject are administered. In certain embodiments, one unit of cord blood or cells obtained therefrom is administered. In certain embodiments, less than one unit is administered. In certain embodiments, more than one unit is administered, e.g., two or more (e.g., 2, 3, 4, 5, 6, or more) units are administered.

4.4. Collection of HT Cells, UCB and Placental Perfusate

HT cells, for example, umbilical cord blood cells, e.g., UCB, and HPCs, e.g., human placental perfusate, can be obtained using methods known in the art and according to procedures established by medical practitioners.

In one embodiment, the umbilical cord or umbilical cord blood and/or placenta is recovered from a patient by informed consent and a complete medical history of the patient prior to, during and after pregnancy is also taken. These medical records can be used to coordinate subsequent use of the placenta or UCB, or the cells, e.g., HPCs or HT cells, for example, UCB cells, harvested therefrom. For example, such human cells obtained from UCB or placental perfusate can then easily be used for personalized medicine for the subject to be treated.

In certain embodiments, human placenta is recovered shortly after its expulsion after birth. In certain embodiments, the cord blood is also recovered. In specific embodiments, the umbilical cord is subjected to a conventional cord blood recovery process. Cord blood may also be obtained from a commercial cord blood banking service, e.g., LifeBankUSA, Cedar Knolls, N.J.

In certain embodiments, umbilical cord blood is collected using an umbilical cord blood collection kit such as described in U.S. Pat. No. 7,147,626, the contents of which are incorporated by reference in their entirety.

In one embodiment, collection kits, containing standard chucks, sterile gauze pad, povidine iodine swabs, sterile alcohol pads, plastic umbilical cord blood clamps, slide clip or hemostat clamps and leak proof resealable bags or canisters are used. The collection can be performed before the placenta is delivered (in utero collection), after the placenta is delivered (ex utero collection) or during a Caesarian section, prior to delivery of placenta. Briefly, the venipuncture site on the distal site on the umbilical cord is sterilized. The collection tubing leading from the large collection bag is clamped, the cap is removed from the needle, and the umbilical vein is cannulated with the bevel of the needle facing down toward the umbilical vein. The clamp is removed to allow the blood to flow and collection bag is lowered below the cannulation site to allow the blood to fill the collection bag by gravity. When the blood flow stops, the venipuncture site is clamped and the needle is withdrawn from the umbilical vein. The collection bag is labeled and put into the insulated shipping container. The placenta with the clamped umbilical cord blood is placed in the leak proof resealable bag and the bag is then properly sealed and labeled. After collection, viability of umbilical cord blood cells is determined by hemocytometer after trypan blue staining.

In certain embodiments, the proximal umbilical cord is clamped, e.g., within 3-4 inches of the insertion into the placental disc prior to cord blood recovery. In other embodiments, the proximal umbilical cord is clamped after cord blood recovery but prior to processing of the placenta. Conventional techniques for the collection of cord blood may be used. In one embodiment, a needle or cannula is used, with the aid of gravity, to drain cord blood.

Methods of perfusing mammalian placentas are disclosed, e.g., in Hariri, U.S. Pat. Nos. 7,045,148 and 7,255,879, and in U.S. Application Publication No. 2007/0190042, entitled "Improved Composition for Collecting and Preserving Organs", the disclosures of which are hereby incorporated by reference herein in their entireties.

In particular embodiments, the placenta may be stored for a period of about 1 hour to about 72 hours or about 4 to about 24 hours, prior to perfusing the placenta to remove any residual cord blood, or prior to perfusing the placenta without removal of residual cord blood. The placenta can be stored in an anticoagulant solution at a temperature of about 5° C. to about 25° C., e.g., at about room temperature. Suitable anticoagulant solutions are well known in the art. For example, a solution of heparin or warfarin sodium can be used. In one embodiment, the anticoagulant solution comprises a solution of heparin (1% w/w in 1:1000 solution). In certain embodiments, the placenta is stored for no more than 36 hours before HPCs, e.g., human placental perfusate, are collected.

In one embodiment, human placental perfusate is obtained by perfusion of the exsanguinated or partially exsanguinated placenta with a suitable aqueous perfusion fluid. In one aspect, the placenta is perfused with a suitable aqueous perfusion fluid without total exsanguination. The perfusion solution can be any aqueous isotonic fluid. In one embodiment, an anticoagulant (e.g., heparin, warfarin sodium) is dissolved in the perfusion solution. Such aqueous isotonic fluids for perfusion are well known in the art, and include, e.g., nutrient media, saline solutions, e.g., phosphate buffered saline or a 0.9 N sodium chloride solution. When used, the perfusion fluid can comprise the anticoagulant at a concentration that is sufficient to prevent the formation of clots of any residual cord blood. In a specific embodiment, a concentration of from 1 to 100 units of heparin is employed. In another specific embodiment, a concentration of 1 to 10 units of heparin per ml is employed. In one embodiment, apoptosis inhibitors, such as free radical scavengers, in particular oxygen free radical scavengers, can be used during and immediately after exsanguination and then these agents can be washed from the placenta. In accordance with this embodiment, the isolated placenta may be stored under hypothermic conditions in order to prevent or inhibit apoptosis.

In certain embodiments, the placenta is not flushed with perfusion fluid to remove all remaining cord blood prior to perfusion. In other embodiments, prior to collection of cells obtained from placental perfusate, the placenta is flushed with, e.g., 10-100 mL of perfusion fluid to remove substantially all remaining cord blood. Typically such flushing is performed by passage of the perfusion fluid through either or both of the umbilical artery and umbilical vein, using a gravity flow into the placenta. The placenta can be oriented (e.g., suspended) in such a manner that the umbilical artery and umbilical vein are located at the highest point of the placenta. In one embodiment, the umbilical artery and the umbilical vein are connected simultaneously, to a pipette that is connected via a flexible connector to a reservoir of the perfusion fluid. The perfusion fluid is passed into the umbilical vein and artery and collected in a suitable open vessel from the surface of the placenta that was attached to the uterus of the mother during gestation. The perfusion fluid may also be introduced through the umbilical cord opening and allowed to flow or percolate out of openings in the wall of the placenta which interfaced with the maternal uterine wall.

In one embodiment, the proximal umbilical cord is clamped during perfusion, e.g., is clamped within 4-6 inches, of the cord's insertion into the placental disc.

In one embodiment, a sufficient amount of perfusion fluid is used that will result in removal of essentially all residual cord blood and, subsequently, collection or recovery of placental cells that remain in the placenta after removal of the cord blood is performed.

In certain embodiments, about 500 milliliters (ml) to 1.5 liters, e.g., 750 ml to 1 liter, of perfusion fluid is adequate to partially or fully exsanguinate the placenta and to recover an initial population of cells, e.g., HPCs or total nucleated cells, but more or less perfusion fluid may be used depending on the observed results.

In a specific embodiment, placental perfusate used in the methods described herein is not free of umbilical cord blood. In a specific embodiment, placental perfusate used in the methods described herein is free of umbilical cord blood. In another specific embodiment, placental perfusate used in the methods described herein is substantially free of umbilical cord blood, e.g., said placental perfusate comprises less than 10%, less than 5%, less than 1%, less than 0.5%, or less than 0.1% cord blood.

In another embodiment, the perfusion solution is passed through the umbilical veins and collected from the umbilical artery, or is passed through the umbilical artery and collected from the umbilical veins. A representative, non-limiting example of such a method can be performed as follows. A post-partum placenta is obtained within about 48 hours after birth. The umbilical cord is clamped and cut above the clamp. The amniotic membrane can be retained during perfusion, or can be separated from the chorion, e.g., using blunt dissection with the fingers. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. An apparatus, e.g., plastic tubing connected to a perfusion device, is then inserted into each of the placental arteries. Plastic tubing, connected to a sterile collection reservoir, e.g., a blood bag such as a 250 mL collection bag, is then inserted into the placental vein. Alternatively, the tubing connected to the apparatus is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate can then be collected, e.g., by centrifugation.

In another particular embodiment, a placenta is placed in a sterile basin and washed with 500 ml of phosphate-buffered normal saline. The wash fluid is then discarded. The umbilical vein is then cannulated with a cannula, e.g., a TEFLON® or plastic cannula, that is connected to a sterile connection apparatus, such as sterile tubing. The sterile connection apparatus is connected to a perfusion manifold. The container containing the placenta is then covered and the placenta is maintained at room temperature (20-25° C.) for a desired period of time, e.g., from 2 to 24 hours, and, in certain embodiments, no longer than 48 hours. The placenta may be perfused continually, with equal volumes of perfusate introduced and effluent perfusate removed or collected. Alternatively, the placenta may be perfused periodically, e.g., at every 2 hours; at 4, 8, 12, and 24 hours; or at other intervals during culturing, with a volume of perfusate, e.g., 100 ml of perfusate (sterile normal saline supplemented with or without 1000 u/l heparin and/or EDTA and/or CPDA (creatine phosphate dextrose)). In the case of periodic perfusion, equal volumes of perfusate can be introduced and removed, so that a stable volume of perfusate bathes the placenta at all times.

The effluent perfusate that escapes the placenta, e.g., at the opposite surface of the placenta, is collected and processed to isolate cells, e.g., HPCs. In specific embodiments, placental cells are isolated from the effluent perfusate using techniques known by those skilled in the art, such as, for example, density gradient centrifugation. In one embodiment, HPCs or total nucleated cells from placental perfusate are isolated by differential centrifugation in order to separate the total nucleated cells from, e.g., cell debris, serum, or enucleated cells. In a specific embodiment, placental cells can be recovered from the effluent perfusate by centrifugation at, e.g., about 5000×g for about 15 minutes at room temperature, which separates cells from contaminating debris and platelets. The cell pellets are resuspended in, e.g., IMDM serum-free medium containing 2 U/ml heparin and 2 mM EDTA (GibcoBRL, NY). The total mononuclear cell fraction can be isolated using apheresis, e.g., using a commercial collection kit such as LYMPHOPREP™ (Nycomed Pharma, Oslo, Norway). Cells may then counted using, e.g., a hemocytometer. Viability is typically evaluated by trypan blue exclusion.

In one embodiment, the isolated placenta is perfused for a period of time without collecting the perfusate, such that the placenta may be perfused for 2, 4, 6, 8, 10, 12, 20 or 24 hours or even days before the perfusate is collected. In such embodiments, for example, perfusion fluid can be introduced into the placenta and allowed to occupy the placental vasculature for a time prior to collection, or in the case of circulated perfusate, the perfusion fluid can be recirculated for such a time.

In one embodiment, perfusion of the placenta and collection of effluent perfusate is repeated once or twice, until the number of recovered nucleated cells falls below 100 cells/ml. The perfusates are pooled and subjected to light centrifugation to remove platelets, debris and de-nucleated cell membranes. The nucleated cells are then isolated by Ficoll-Hypaque density gradient centrifugation In other embodiments, the cells collected from the placenta are cryopreserved for use at a later time. Methods for cryopreservation of cells, such as stem cells, are well known in the art, for example, cryopreservation using the methods of Boyse et al. (U.S. Pat. No. 5,192,553, issued Mar. 9, 1993) or Hu et al. (WO 00/73421, published Dec. 7, 2000).

5. EXAMPLES

5.1. Example 1: Transplantation of Unrelated Cord Blood and Unmatched Mononuclear Cells from Human Placental Perfusate in a Patient with a Metabolic Disorder This example illustrates the safe, successful administration of unrelated umbilical cord blood (UCB) and unmatched mononuclear cells from human placental perfusate to a patient with a metabolic disorder.

The patient was a 11 year old male with adrenoleukodystrophy (ALD), aggressive mutation. The patient received reduced toxicity conditioning at around day −8. At day 0, the patient received a transplant, by infusion, of a single unit of unrelated UCB and unrelated (to either the patient recipient or to the UCB), unmatched mononuclear cells from human placental perfusate. In particular, the patient received a single UCB donor product (6/6 HLA match; approximately $3.9 \times 10^7$ total cells/kg; approximately $2.8 \times 10^5$ CD34$^+$ cells/kg) and combined total nucleated cell dose (TNC) from perfusate of approximately $0.6 \times 10^7$ cells/kg (approximately $0.3 \times 10^5$ CD34$^+$ cells/kg).

At 140 days after transplant: 1) the patient exhibited full engraftment of UCB with 99% UCB transplant donor chimerism and 0% placental perfusate cell chimerism, as assayed in blood; 2) the patient showed no evidence of GVHD; and 3) the patient showed no signs of neurodegeneration, a symptom of the ALD. Testing for chimerism was first performed between 28 and 42 days after transplant.

These results indicate that a single UCB transplant combined with infusion of unmatched unrelated mononuclear cells from human placental perfusate in a child with non-malignant disease is safe and well tolerated. Moreover, although by the time of the latest timepoint assayed (140 days post-transplant), detection of neurodegeneration would have been expected in such an ALD patient, no neurodegeneration was actually detected.

5.2. Example 2: Transplantation of Unrelated Cord Blood and Unmatched Mononuclear Cells from Human Placental Perfusate in a Patient with Malignant Disease (#1)

This example illustrates the safe, successful administration of unrelated umbilical cord blood (UCB) and unmatched unrelated mononuclear cells from human placental perfusate to a patient with a malignant disease, acute lymphoblastic leukemia (ALL).

The patient was a 22 year old female with ALL. Prior to administration of unrelated UCB and unmatched unrelated mononuclear cells from human placental perfusate, the patient had undergone previous chemotherapy, and received reduced toxicity conditioning at around day −8. At the time of administration of unrelated UCB and unmatched unrelated mononuclear cells from human placental perfusate, the patient exhibited complete myeloablation. At day 0, the patient received double, unrelated cord UCB units (both units were 5/6 HLA matched; one unit contained approximately $3 \times 10^7$ cells/kg (approximately $1.9 \times 10^5$ CD34$^+$ cells/kg), and the other contained approximately $2.5 \times 10^7$ total cells/kg (approximately $1.42 \times 10^5$ CD34$^+$ cells/kg)) and unmatched, unrelated (with respect to either the patient recipient or to the UCB) nucleated cells from human placental perfusate (TNC of approximately $0.4 \times 10^7$ cells/kg; approximately $0.4 \times 10^5$ CD34$^+$ cells/kg).

Engraftment of cells from both UCB units and perfusate cells was detected by day 23. At 70 days after transplant, the patient continued to exhibit full engraftment, with 65%/34%/1% UCB (unit #1/unit #2)/placental perfusate cell donor chimerism, as assayed in blood. Additionally, despite the fact that post-ablation the patient retained an approximately 1% immune system, the patient exhibited no GVHD. At last assessment (greater than 100 days after transplant), the patient was alive.

These results indicate that a double, partially unmatched UCB transplant combined with infusion of unmatched unrelated mononuclear cells from human placental perfusate in a patient with malignant disease is safe and well tolerated.

5.3. Example 3: Transplantation of Unrelated Cord Blood and Unmatched Mononuclear Cells from Human Placental Perfusate in a Patient with Malignant Disease (#2)

This example is designed to assess the administration of unmatched unrelated umbilical cord blood (UCB) and unmatched unrelated mononuclear cells from human placental perfusate to a patient with a malignant disease, acute lymphoblastic leukemia (ALL).

The patient was a 17 year old female with ALL in CR1 (induction failure). The patient received myeloablative conditioning or reduced toxicity conditioning at around day −8. At day 0, the patient received double, unrelated cord UCB units (both were 4/6 HLA matched; one unit contained approximately $2.7 \times 10^7$ cells/kg (approximately $3.6 \times 10^5$ CD34$^+$ cells/kg), and the other contained approximately $2.7 \times 10^7$ cells/kg (approximately $2.5 \times 10^5$ CD34$^+$ cells/kg)) and unmatched, unrelated (with respect to either the patient recipient or to the UCB) mononuclear cells from human placental perfusate (TNC of approximately $0.3 \times 10^7$ cells/kg; approximately $0.2 \times 10^5$ CD34$^+$ cells/kg). Engraftment was detected and the patient exhibited no safety events. At last assessment (day 60 after transplant), the patient had not exhibited any grade III or IV GVHD.

5.4. Example 4: Clinical Protocol for Transplantation of Unrelated and Related Umbilical Cord Blood in Combination with Human Mononuclear Placental Perfusate Cells The protocol presented herein is a single arm, non-randomized pilot study whose primary objective is to assess the safety of transplantation with human mononuclear placental perfusate cells combined with cord blood in Groups A-D, below, with various malignant or nonmalignant disorders who require a stem cell transplant. A secondary objective of this study is to assess hematopoietic engraftment, donor chimerism and immune function in subjects with various malignant or nonmalignant disorders potentially curable with stem cell transplantation.

The following groups are utilized in the study:

Group A: (three subjects) Partially unmatched related cord blood with ≥3/6 HLA match to the patient and related perfusate cells. UCB and perfusate cells are from the same donor and the donor is related to the patient.

Group B: (twelve subjects) Unrelated cord blood with ≥4/6 HLA match to the patient and unrelated perfusate cells. UCB is from an unrelated donor and the perfusate cells are from a separate unrelated donor.

Group C: (three subjects) Unrelated cord blood with ≥4/6 HLA match to the patient but related to perfusate cells. UCB and perfusate cells are from the same donor however the donor is not related to the patient.

Group D: (twelve subjects) Double unrelated cord blood units with ≥4/6 HLA match to patient and each other and unrelated perfusate cells. Each UCB unit is from a separate and unrelated partially unmatched donor to the patient and the perfusate cells donor is unrelated to the patient or either of the UCB donors.

All subjects undergo either full myeloablation or reduced toxicity pre-transplant conditioning, as dictated by the disorder for which the transplant is indicated, followed by transplantation with UCB and infusion of perfusate cells. UCB infusion(s) are administered utilizing standard procedures. After a four-hour wait period, to ensure that there are no ongoing toxicities from the UCB infusion, there is an infusion of one unit perfusate cells (such a unit must contain a sufficient number of cells such that the subject can receive≥$2.5\times10^6$ TNC/kg body weight). The perfusate cell unit is thawed and infusion occurs within 90 minutes from the start of thawing. Standard of care GVHD prophylaxis is also administered.

During the conduct of this study, the occurrence of all adverse clinical and laboratory events will be collected, with an emphasis on assessing incidence of GVHD in each of Group A-D during the first 100 days following transplantation, and any incidence of acute transfusion reactions (occurring during or within 24 hours of the transfusion). Subjects are evaluated at baseline, during the pre-transplant conditioning period, at the time of transplant, and for at least 6 months post-transplant. To safeguard subject safety, a temporary enrollment hold will be triggered by the appearance of one or more index serious adverse events in any subject enrolled in the study.

Inclusion Criteria:

Key Inclusion Criteria for all subjects regardless of diagnosis include: 1) subject, parent or legal guardian must understand and voluntarily sign an informed consent form; 2) subject must understand and sign an age appropriate assent form (if applicable); 3) must be ≤55 years of age at the time of signing the informed consent form; 4) must be able to adhere to the study visit schedule and other protocol requirements; 5) a female of childbearing potential (FCBP) must have a negative serum or urine pregnancy test within seven days of starting preconditioning; 6) a sexually active FCBP must agree to use adequate contraceptive methods while on study therapy; 7) life expectancy greater than 3 months; 8) appropriate general health status including: a) Lansky performance status≥50% (children) or Karnofsky performance status≥70% (adults) or ECOG performance status 0-2 (adults); b) corrected DLCO≥50 percent predicted; c) left ventricular ejection fraction≥40% estimated; d) creatinine clearance or estimated GFR≥60 mL/min/1.73 $m^2$; e) serum bilirubin≤1.5× upper limit of normal; f) transaminases≥3× upper limit of normal; g) absence of uncontrolled infection; and h) HIV negative. Additional inclusion criteria specific for the disease or disorder exhibited by the subject will also be satisfied.

Exclusion Criteria:

Subjects will be ineligible for this study if they meet any one of the following criteria: 1) any medical condition, laboratory abnormality, or psychiatric illness that would impose excessive risk to the patient or would adversely affect his/her participating in this study or confound the ability to interpret data from the study; 2) patients with Fanconi Anemia are ineligible for this study; 3) myocardial infarction within 6 months prior to enrollment; 4) New York Heart Association (NYHA) Class III or IV heart failure; 5) uncontrolled angina; 6) severe uncontrolled ventricular arrhythmias; 7) electrocardiographic evidence of acute ischemia or active conduction system abnormalities; 8) uncontrolled infection; 9) major anticipated illness or organ failure incompatible with survival from stem cell transplant; 10) pregnant or breast-feeding females; 11) subject has received other investigational agents within 30 days prior to the start of the conditioning regimen.

UCB and Perfusate Cell Requirements:

1) a single related cord blood unit must contain ≥$3.5\times10^7$ TNC/kg body weight for 5/6 and 6/6 HLA matched and ≥$5.0\times10^7$ TNC/kg for 3/6 and 4/6 HLA matched pre thaw (Group A); 2) a single unrelated UCB unit must contain ≥$3.5\times10^7$ TNC/kg body weight for 5/6 HLA match or 6/6 HLA match or ≥$5.0\times10^7$ TNC/kg body weight for 4/6 HLA match (pre-thaw) (Group B); 3) a single unrelated cord blood units must contain ≥$5.0\times10^7$ TNC/kg body weight and 4/6, 5/6 or 6/6 HLA matched pre thaw (Group C); 4) double unrelated cord blood units must contain ≥$5.0\times10^7$ TNC/kg combined for both units (pre-thaw) and be ≥4/6 HLA matched to each other and recipient (Group D); 5) HPC unit must contain a sufficient number of cells such that the subject can receive ≥$2.5\times10^6$ TNC/kg body weight.

HLA Typing and HLA Match Grade:

1) Unrelated Cord Blood/Matched Family Donors: HLA typing is performed by serology for Class I A and B and by high resolution DNA typing of DRB1; 2) family donors must be first generation relatives matched at 5/6 or 6/6 HLA A and B (Class I) antigens by serology and HLA DRB1 (Class II) antigens by DNA typing; 3) single related cord blood unit must contain: ≥$3.5\times10^7$ TNC/kg body weight for 5/6 and 6/6 HLA matched and ≥$5.0\times10^7$ TNC/kg for 3/6 and 4/6 HLA matched pre thaw (Group A); 4) single unrelated UCB unit must contain ≥$3.5\times10^7$ TNC/kg body weight for 5/6 HLA match or 6/6 HLA match or ≥$5.0\times10^7$ TNC/kg body weight for 4/6 HLA match (pre-thaw) (Group B); 5) single unrelated cord blood units must contain ≥$5.0\times10^7$ TNC/kg body weight and 4/6, 5/6 or 6/6 HLA matched pre thaw (Group C); 6) double unrelated cord blood units must contain ≥$5.0\times10^7$ TNC/kg combined for both units (pre-thaw) and be ≥4/6 HLA matched to each other and recipient (Group D); 7) for double unrelated cord blood transplantation, the first unit selected will be the best available HLA-matched cord blood unit (≥4/6 with the patient) and ≥4/6 with each other unit.

All subjects will undergo rigorous safety assessments during the pre-transplant conditioning period, at the time of transplant, and post-transplant for up to 6 months. The key assessments performed include physical examinations, hematology and clinical chemistry determinations, bone marrow aspirates, bone marrow biopsies and peripheral blood analyses, radiologic examinations and full monitoring of adverse events with special emphasis on GVHD, toxicity, and infections.

Hematologic evaluations for Neutrophil and Platelet Engraftment:

A complete blood count with differential is performed every 1-3 days from Day 0 to absolute neutrophil count >500/$mm^3$ for 3 days after nadir is reached and until platelet count reaches 20,000/$mm^3$ for 3 consecutive measurements on 3 different days and independence from platelet transfusion for a minimum of 7 days. Neutrophil and platelet engraftment studies will be recorded on the appropriate pages of the CRF. "Neutrophil engraftment" refers to the first of three days following the neutrophil nadir with an absolute neutrophil count above 500/$mm^3$. "Platelet engraftment" refers to the first of three consecutive days demonstrating a platelet count≥20,000/mm³, after a seven day period of platelets≥20,000/mm³ without transfusions.

Donor Chimerism:

Quantitation of peripheral blood donor chimerism (UCB/s and perfusate cells)(whole blood, NK and T Cell) is assessed on Days 7, 14, 30, 60, 100 and 180 (+/−10 days). In addition, quantitation of peripheral blood recipient chimerism is assessed at baseline along with chimerism of the donor cells (UCB and perfusate cells) at baseline. Quantitation is performed using short tandem repeat assays.

Bone Marrow Aspirates, Bone Marrow Biopsies and Peripheral Blood Analyses:

Bone marrow aspirates and biopsies are performed according to accepted procedures for the underlying disease to assess subjects' disease status. It is expected that these analyses are performed at Day 100 and 180 post transplant, ±10 days.

EQUIVALENTS

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed:

1. A method of transplanting human umbilical cord blood (UCB) cells to a subject, said method comprising administering UCB cells in combination with a population of mononuclear cells from human placental perfusate, wherein: said mononuclear cells from human placental perfusate are not matched to the subject, wherein said method reduces the duration or severity of graft versus host disease.

2. The method of claim 1, wherein said UCB cells are not related to said mononuclear cells from placental perfusate.

3. The method of claim 2, wherein said UCB cells are not matched to said mononuclear cells from placental perfusate.

4. The method of claim 2, wherein said UCB cells are not related or matched to said mononuclear cells from placental perfusate.

5. The method of claim 2, wherein said UCB cells are 3/6 to 6/6 HLA matched to the subject.

6. The method of claim 2, wherein one unit of UCB cells is administered.

7. The method of claim 2, wherein greater than one unit of UCB cells is administered.

8. The method of claim 2, wherein said UCB cells are present in UCB.

9. The method of claim 2, wherein said mononuclear cells from placental perfusate are present in placental perfusate.

10. The method of claim 2, wherein the placental perfusate is obtained from a placenta that has been partially exsanguinated.

11. The method of claim 2, wherein 2% or greater of the placental perfusate cells are CD34+.

12. The method claim 2, wherein said method results in chimerism in the subject.

13. The method of claim 12, said chimerism comprising UCB cells or progeny therefrom, placental perfusate cells or progeny therefrom, or both UCB cells or progeny therefrom and placental perfusate cells or progeny therefrom.

14. The method of claim 12, wherein greater than one unit of UCB cells is administered and wherein said method results in chimerism in the subject, said chimerism comprising cells from greater than one unit of UCB cells or progeny therefrom.

15. The method of claim 12, said chimerism comprising placental perfusate cells or progeny therefrom.

16. The method of claim 2, wherein said method results in engraftment of UCB cells, placental perfusate cells, or both UCB cells and placental perfusate cells.

17. The method of claim 2, wherein said subject has a tumor and said method results in a graft versus tumor reaction.

18. The method of claim 2, wherein said method results in amelioration of a symptom of: a) a metabolic disorder such as adrenoleukodystrophy, mucopolysaccharidosis, Niemann-Pick disease, metachromatic leukodystrophy, Wolman disease, Krabbe's disease, Gaucher's disease, fucosidosis, or Batten disease in a subject in need thereof; or b) a hematologic disorder or malignancy, such as myelodysplastic syndrome, amegakaryocytic thrombocytopenia, acute lymphoblastic leukemia, acute myelogenous leukemia, sickle cell disease, beta thalassemia, severe combined immunodeficiency disease, marrow failure, or anemia such as severe aplastic anemia or Diamond-Blackfan anemia in a subject in need thereof.

19. The method of claim 2, wherein the subject is a human subject.

20. The method of claim 19, wherein the human subject is 25 years old or younger.

* * * * *